United States Patent
Baril et al.

(10) Patent No.: US 11,452,540 B2
(45) Date of Patent: Sep. 27, 2022

(54) WIRELESS TISSUE DISSECTOR

(71) Applicant: Covidien LP, Mansfield, MA (US)

(72) Inventors: Jacob C. Baril, Norwalk, CT (US);
Matthew A. Dinino, Newington, CT (US); Saumya Banerjee, Hamden, CT (US); George Matta, Plainville, MA (US); Justin Thomas, New Haven, CT (US); Roy J. Pilletere, North Haven, CT (US)

(73) Assignee: Covidien LP, Mansfield, MA (US)

( * ) Notice: Subject to any disclaimer, the term of this patent is extended or adjusted under 35 U.S.C. 154(b) by 58 days.

(21) Appl. No.: 16/854,339

(22) Filed: Apr. 21, 2020

(65) Prior Publication Data

US 2020/0375625 A1    Dec. 3, 2020

Related U.S. Application Data

(60) Provisional application No. 62/854,478, filed on May 30, 2019.

(51) Int. Cl.
*A61B 17/3205* (2006.01)
*A61B 17/32* (2006.01)
*A61B 17/00* (2006.01)

(52) U.S. Cl.
CPC .... *A61B 17/3205* (2013.01); *A61B 17/32053* (2013.01); *A61B 2017/00415* (2013.01); *A61B 2017/00734* (2013.01); *A61B 2017/320044* (2013.01)

(58) Field of Classification Search
CPC .............. A61B 17/32053; A61B 17/32; A61B 17/320758; A61B 17/32002; A61B 2017/320024; A61B 2017/00734
See application file for complete search history.

(56) References Cited

U.S. PATENT DOCUMENTS

| | | | |
|---|---|---|---|
| 6,048,345 A * | 4/2000 | Berke | A61B 17/1624 606/171 |
| 7,384,423 B1 | 6/2008 | Chin | |
| 8,668,710 B2 | 3/2014 | Slipszenko et al. | |
| 9,492,190 B2 | 11/2016 | Brannan et al. | |
| 2011/0250562 A1* | 10/2011 | Tanaka | A61C 1/185 433/130 |
| 2013/0006242 A1 | 1/2013 | Koss | |
| 2015/0216551 A1* | 8/2015 | Dieras | A61C 1/07 606/169 |

FOREIGN PATENT DOCUMENTS

WO    2011156606 A1    12/2011
WO    2014052809 A1    4/2014

* cited by examiner

*Primary Examiner* — Sarah A Simpson
(74) *Attorney, Agent, or Firm* — Carter, DeLuca & Farrell LLP (57) ABSTRACT

A tissue dissector includes a handle portion and a head portion. The handle portion includes an actuation assembly having an actuator. The head portion includes an annular body having a blade assembly rotatably supported in the annular body. The blade assembly includes a blade member defining an aperture configured to receive tissue therethrough. The blade member is operatively coupled with the actuator for rotation about a central axis defined by the aperture. The handle portion and the head portion define a longitudinal axis that is disposed at an angle relative to the central axis.

9 Claims, 14 Drawing Sheets

WIRELESS TISSUE DISSECTOR

CROSS-REFERENCE TO RELATED APPLICATION

This application claims priority to and the benefit of U.S. Provisional Application No. 62/854,478 filed May 30, 2019. The disclosure of the foregoing application is hereby incorporated by reference in its entirety herein.

BACKGROUND

Technical Field

The present disclosure relates generally to the field of tissue cutting and removal. In particular, the present disclosure relates to a wireless tissue dissector.

Background of Related Art

Surgical cutting instruments in which an elongate inner member is rotated within an elongate, tubular outer member are utilized in surgical procedures where access to the surgical site is gained via a narrow portal or passage. Typically, the tubular outer member includes a distal end with an opening defining a cutting port or window and the inner member includes a distal end with a cutting tip for engaging bodily tissue via the opening. Proximal ends of the inner and outer members commonly include hubs which attach to a handpiece having a motor for rotating the inner member relative to the outer member. The distal end of the inner member may have various configurations dependent upon the surgical procedure to be performed, with the opening in the distal end of the outer member being suitably configured to cooperate with the particular configuration of the distal end of the inner member to cut, resect, and/or abrade tissue. Often the inner member is tubular so that the loose tissue resulting from a cutting, resecting, and/or abrading procedure can be aspirated through the hollow lumen of the inner member.

SUMMARY

As used herein, the term "distal" refers to the portion that is described which is farther from a user, while the term "proximal" refers to the portion that is described which is closer to a user. Further, to the extent consistent, any or all of the aspects described herein may be used in conjunction with any or all of the other aspects described herein.

In accordance with an aspect of the present disclosure a tissue dissector includes a handle portion and a head portion. The handle portion includes an actuation assembly having an actuator. The head portion includes an annular body having a blade assembly rotatably supported in the annular body. The blade assembly includes a blade member defining an aperture configured to receive tissue therethrough. The blade member is operatively coupled with the actuator for rotation about a central axis defined by the aperture. The handle portion and the head portion define a longitudinal axis that is disposed at an angle relative to the central axis.

In another aspect, the blade assembly may further include a blade gear secured with the blade member for concomitant rotation therewith. The blade gear may be operatively coupled with the actuator of the actuation assembly.

In yet another aspect, the blade member may include a support portion and a blade portion extending from the support portion. The support portion may be in a planar contact with the blade gear.

In still yet another aspect, the blade portion may have a frusto-conical shape.

In still yet another aspect, the actuation assembly may further include a transmission gear coupled with an output shaft of the actuator and configured to engage the blade gear such that actuation of the actuator imparts rotation to the blade member.

In another aspect, the head portion may further include inner and outer walls defining a circular groove therebetween. At least a portion of the blade gear may be rotatably disposed within the circular groove.

In yet another aspect, the head portion may include a plurality of axial bearings circumferentially arranged in the circular groove of the head portion. The blade gear may be rotatably supported in the circular groove.

In still yet another aspect, the head portion may further include a plurality of second bearings configured to engage the blade gear. The plurality of second bearings may be disposed substantially parallel to an axis extending through the aperture of the blade member.

In still yet another aspect, the blade gear may be rotatably interposed between the plurality of axial bearings and the plurality of second bearings.

In still yet another aspect, the head portion may further include a third bearing configured to engage the blade portion of the blade member. The third bearing may define an acute angle with respect to an axis extending through the aperture.

In another aspect, the handle portion may further define a battery pack to supply power to the actuator.

In yet another aspect, the battery pack may be removably disposed within the handle portion.

In accordance with another aspect of the present disclosure, a tissue dissector includes a handle portion and a head portion. The handle portion includes a motor, a motor pulley operatively coupled with an output shaft of the motor, and a belt. The handle portion defines a longitudinal axis. The head portion includes a blade assembly including an annular blade pulley and an annular blade member secured with the annular blade pulley for concomitant rotation therewith. The belt may be operatively coupled with the annular blade pulley and the motor pulley such that actuation of the motor drives the annular blade pulley, which, in turn, rotates the annular blade member about a central axis disposed at an angle relative to the longitudinal axis of the handle portion. The annular blade member and the annular blade pulley are configured to receive tissue therethrough.

In an aspect, the annular blade member may include a support portion in a planar contact with the annular blade pulley.

In another aspect, the handle portion may further include a tensioner assembly to provide tension in the belt.

In yet another aspect, the annular blade member may further include a switch configured to actuate the motor.

In still yet another aspect, the annular blade member may include a blade edge configured to cut tissue.

In accordance with yet another aspect of the present disclosure, a tissue dissector includes a handle portion and a blade assembly. The handle portion includes an actuation assembly and defines a longitudinal axis. The blade assembly is configured to be partially received within an opening in tissue. The blade assembly includes an annular blade member defining an aperture configured to receive tissue therethrough. The annular blade member includes an edge portion configured to rotatably cut tissue. The actuation assembly is operatively coupled with the annular blade member to impart rotational output to the annular blade member. The annular blade member is rotatable about a central axis disposed substantially orthogonal to the longitudinal axis of the handle portion.

BRIEF DESCRIPTION OF THE DRAWINGS

Various aspects and features of the present disclosure are described hereinbelow with reference to the drawings wherein like numerals designate identical or corresponding elements in each of the several views and.

DETAILED DESCRIPTION

Embodiments of the present disclosure are described in detail with reference to the drawings, in which like reference numerals designate identical or corresponding elements in each of the several views.

Figure 1:
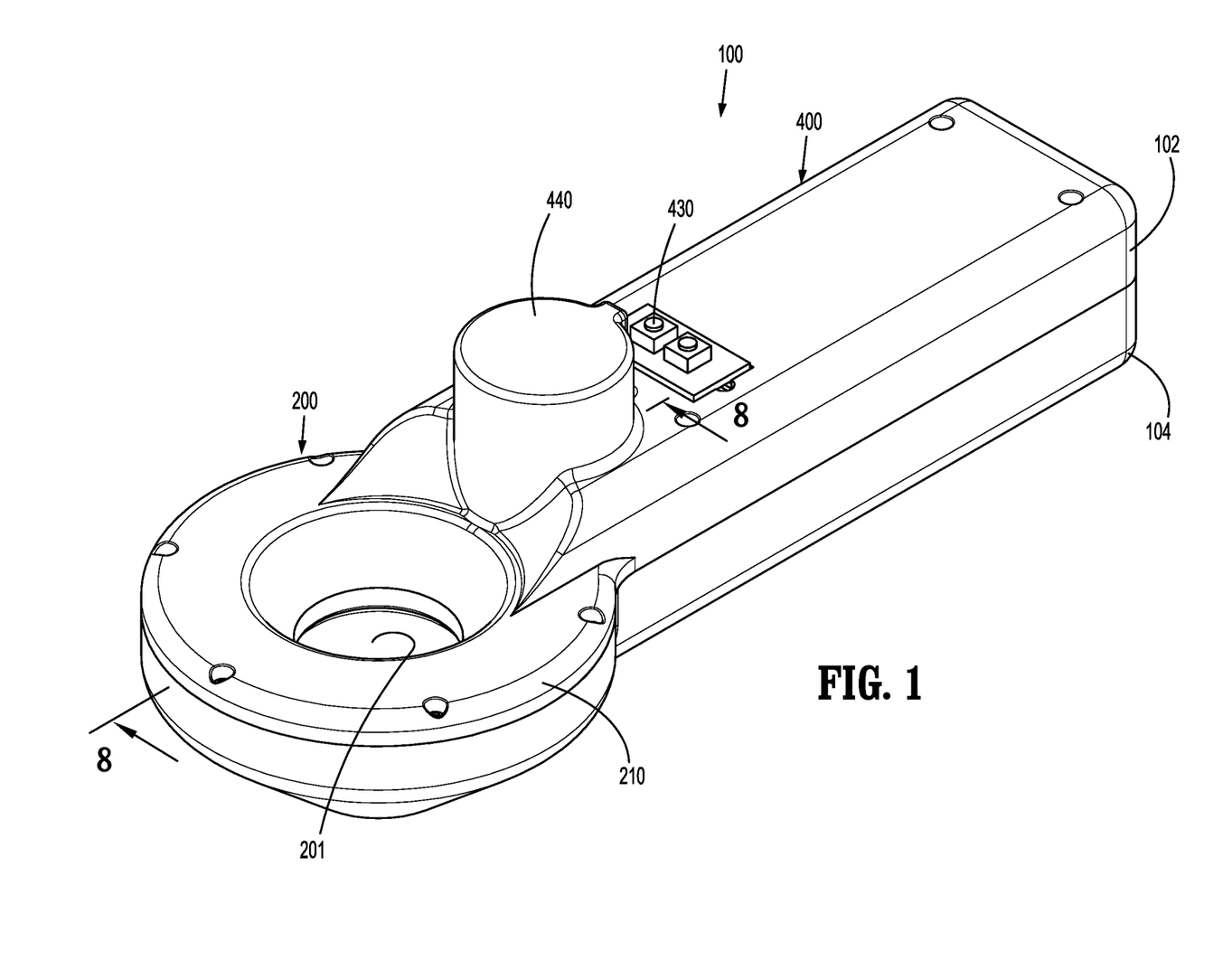
FIG. 1 is a perspective view of a tissue dissector in accordance with the present disclosure.
Figure 2:
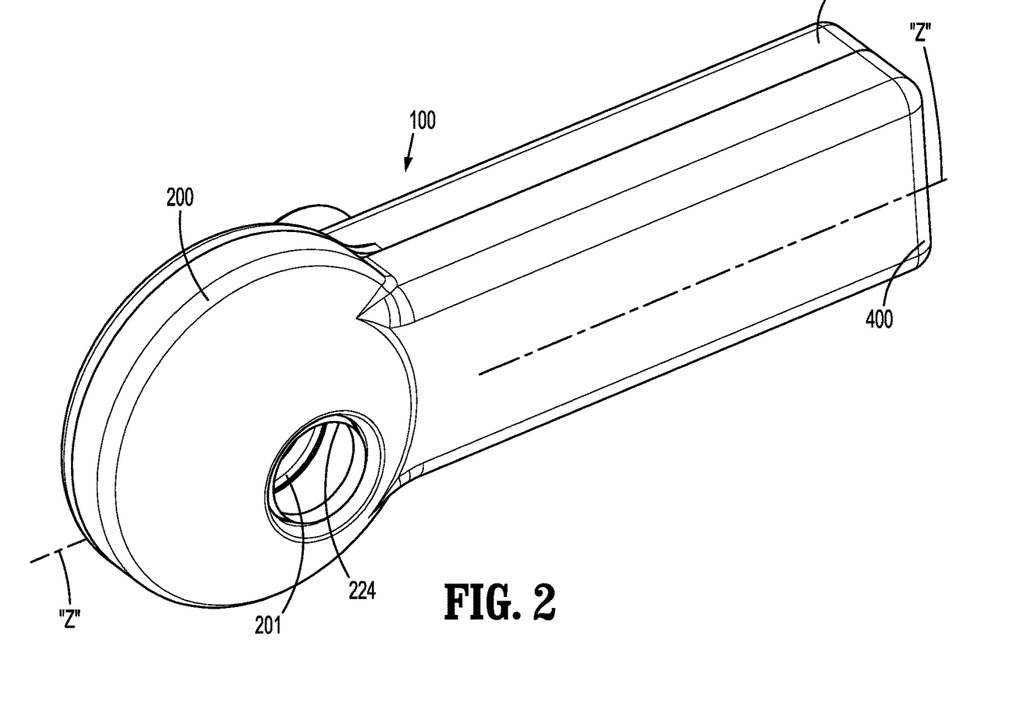
FIG. 2 is a bottom perspective view of the tissue dissector of FIG. 1.

With reference to FIGS. 1 and 2, there is provided a tissue dissector 100 for extracting tissue from a patient. The tissue dissector 100 includes housing halves 102, 104 configured to support a blade assembly 250 (FIG. 3) and an actuation assembly 410. The tissue dissector 100 includes a dissector head portion 200 including the blade assembly 250 (FIG. 3), and a handle portion 400 including the actuation assembly 410. In particular, the dissector head portion 200 includes an annular body 210 extending from the handle portion 400.

The annular body 210 defines an aperture 201 configured to receive tissue therethrough. For example, the annular body 210 may be tapered to facilitate extraction of tissue from the surgical site through the dissector head portion 200. The handle portion 400 is ergonomically designed to be gripped by a clinician such that the clinician may easily access actuation buttons 430 to actuate the actuation assembly 410. Further, the dissector head portion 200 and handle portion 400 cooperate to define a common longitudinal axis that is disposed at an angle relative to a central axis defined through aperture 201. The angle may be, in embodiments, 90 degrees (such that the axes are perpendicular). In other embodiments, the angle may be from about 45 degrees to about 90 degrees, in other embodiments from about 60 degrees to about 90 degrees, and in still other embodiments, from about 75 degrees to about 90 degrees. In this manner, tissue is extracted from the surgical site through the tissue dissector at an angle, e.g., 90 degrees or an angle from about 45 degrees to about 90 degrees, relative to the longitudinal axis defined by the dissector head portion 200 and handle portion 400.

Tissue dissector 100 may be configured as a single-use device that is discarded after use or sent to a manufacturer for reprocessing, a reusable device capable of being cleaned and/or sterilized for repeated use by the end-user, or a partially-single-use, partially-reusable device. With respect to partially-single-use, partially-reusable configurations, the handle portion 400 may be configured as a cleanable/sterilizable, reusable component, while the dissector head portion 200 is configured as a single-use, disposable/reprocessable component. Under such a configuration, the dissector head portion 200 is configured to releasably engage the handle portion 400 to facilitate disposal/reprocessing of any single-use components and cleaning and/or sterilization of any reusable components. Further, enabling releasable engagement of the dissector head portion 200 with the handle portion 400 allows for use of different dissector head portions 200 with the handle portion 400.

Figure 3:
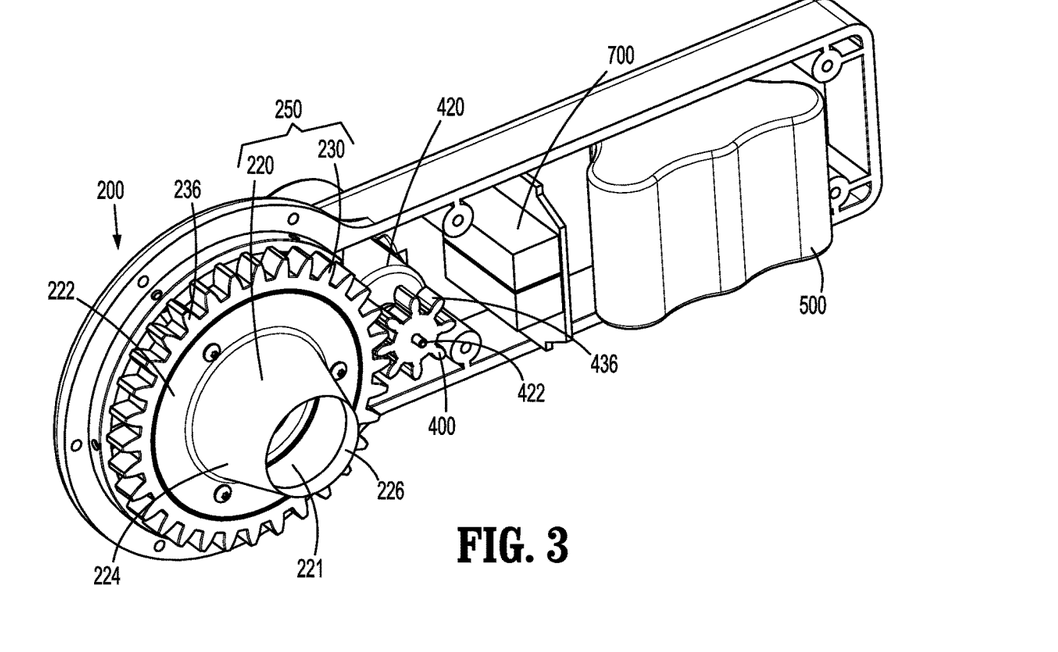
FIG. 3 is a bottom perspective view of the tissue dissector of FIG. 2 with a bottom housing half removed.
Figure 4:
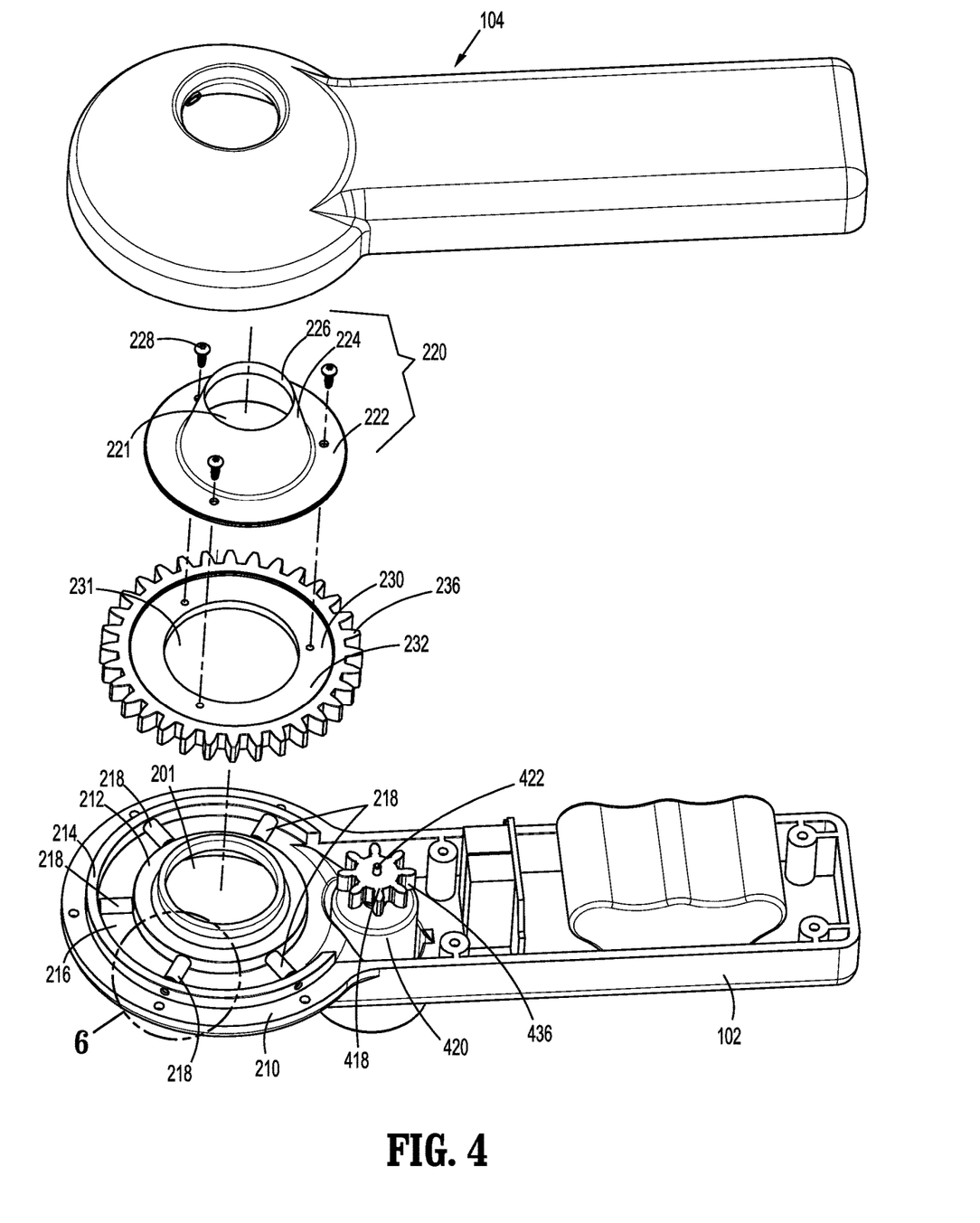
FIG. 4 is a perspective view of the tissue dissector of FIG. 1 with parts of a blade assembly separated.

With reference now to FIGS. 3 and 4, the dissector head portion 200 includes the annular body 210 (FIG. 1) configured to support the blade assembly 250. The blade assembly 250 includes a blade member 220 including a support portion 222, a blade portion 224 having e.g., a frusto-conical, shape, and a blade edge 226 configured to cut tissue. In particular, the blade member 220 defines an opening 221 in communication (and axial alignment) with the aperture 201 (FIG. 2) of the dissector head portion 200 and is configured to receive tissue therethrough. The blade assembly 250 further includes a blade gear 230 coupled with the blade member 220 for concomitant rotation therewith. In particular, the blade member 220 may be concentrically secured to the blade gear 230 via, e.g., adhesive, ultrasonic welding or a plurality of screws 228. In this manner, the blade gear 230 operatively couples the blade member 220 to a motor 420 of the actuation assembly 410. The blade gear 230 includes a coupling portion 232 configured to engage the support portion 222 of the blade member 220 such that the blade portion 224 extends away, e.g., distally, from the blade gear 230. In addition, the blade gear 230 defines an opening 231 in communication with the opening 221 of the blade member 220. The blade gear 230 further includes a plurality of teeth 236 circumferentially arranged around the blade gear 230 and disposed radially outward of the coupling portion 232. In this manner, the support portion 222 of the blade member 220 is disposed radially inward of the plurality of teeth 236. The plurality of teeth 236 is configured to operatively engage a plurality of teeth 436 of a transmission gear 418 supported on an output shaft 422 of the motor 420 of the actuation assembly 410. In this manner, rotational output of the motor 420 is imparted via the transmission gear 418 to the blade gear 230, which, in turn, causes rotation of the blade member 220.

With particular reference to FIG. 4, the blade gear 230 is rotatably supported in the annular body 210. In particular, the annular body 210 includes inner and outer walls 212, 214 that are concentrically disposed and configured to support a plurality of axial bearings 218. The plurality of axial bearings 218 is circumferentially arranged about the aperture 201 defined in the annular body 210. In particular, each axial bearing 218 is supported between the inner and outer walls 212, 214 and is rotatably supported within a circumferential groove 216 defined between the inner and outer walls 212, 214. In this manner, the plurality of axial bearing 218 enable rotation of the blade gear 230 supported thereon.

Figure 5:
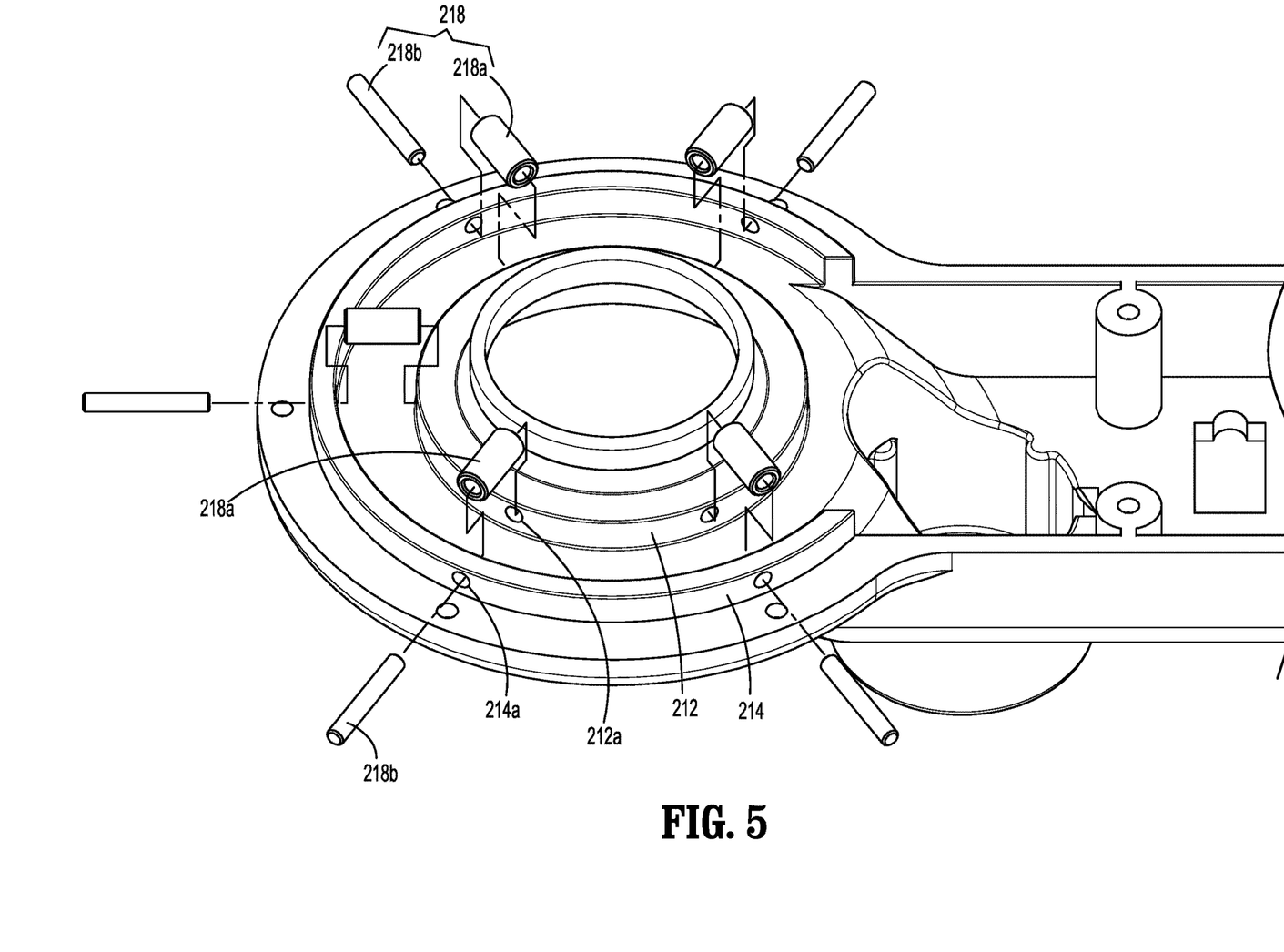
FIG. 5 is another bottom perspective view of the tissue dissector of FIG. 1 with a bottom housing half removed.
Figure 6:
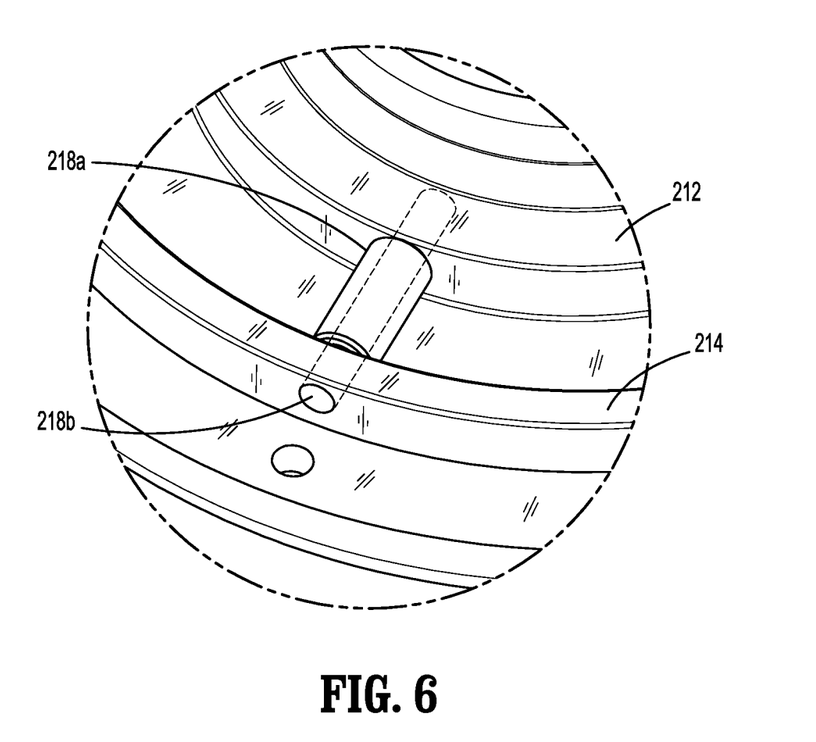
FIG. 6 is an enlarged perspective view of the area of detail of FIG. 4.
Figure 7:
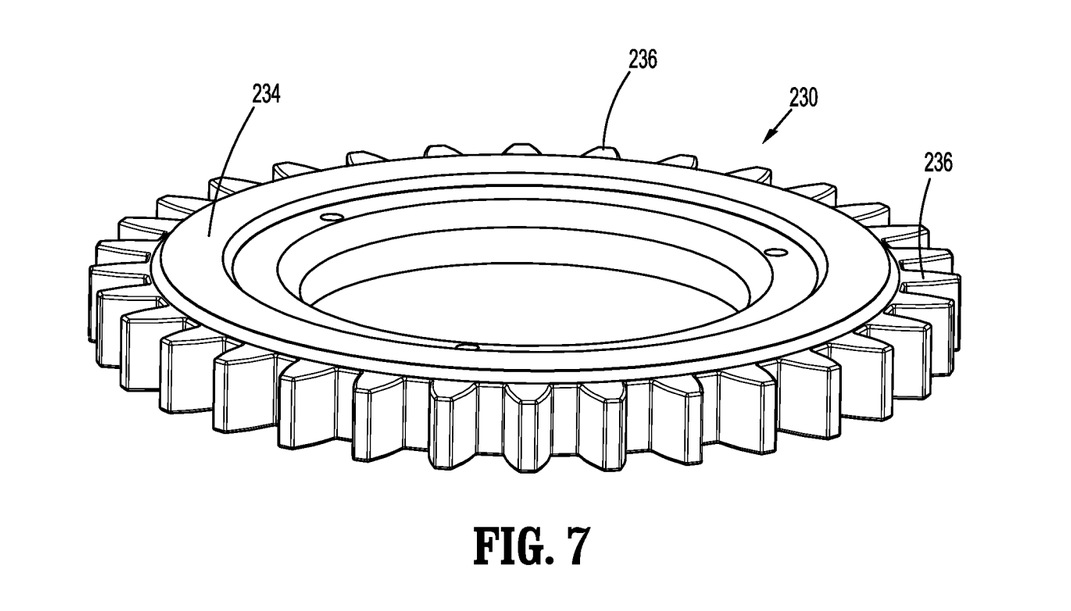
FIG. 7 is a perspective view of a blade gear of the tissue dissector of FIG. 1.

With reference now to FIGS. 5 and 6, each axial bearing 218 includes a pin 218b supported in bores 212a, 214a defined in the respective inner and outer walls 212, 214, and a bearing sleeve 218a rotatably supported on the pin 218b. With reference now to FIG. 7, the blade gear 230 further includes a bearing surface 234 configured to engage the plurality of axial bearings 218. In particular, the bearing surface 234 may be raised from, e.g., a plane, defined by the plurality of teeth 236 such that the bearing surface 234 is at least partially disposed within the groove 216 (FIG. 4) defined between the inner and outer walls 212, 214 to guide rotation of the blade gear 230.

Figure 8:
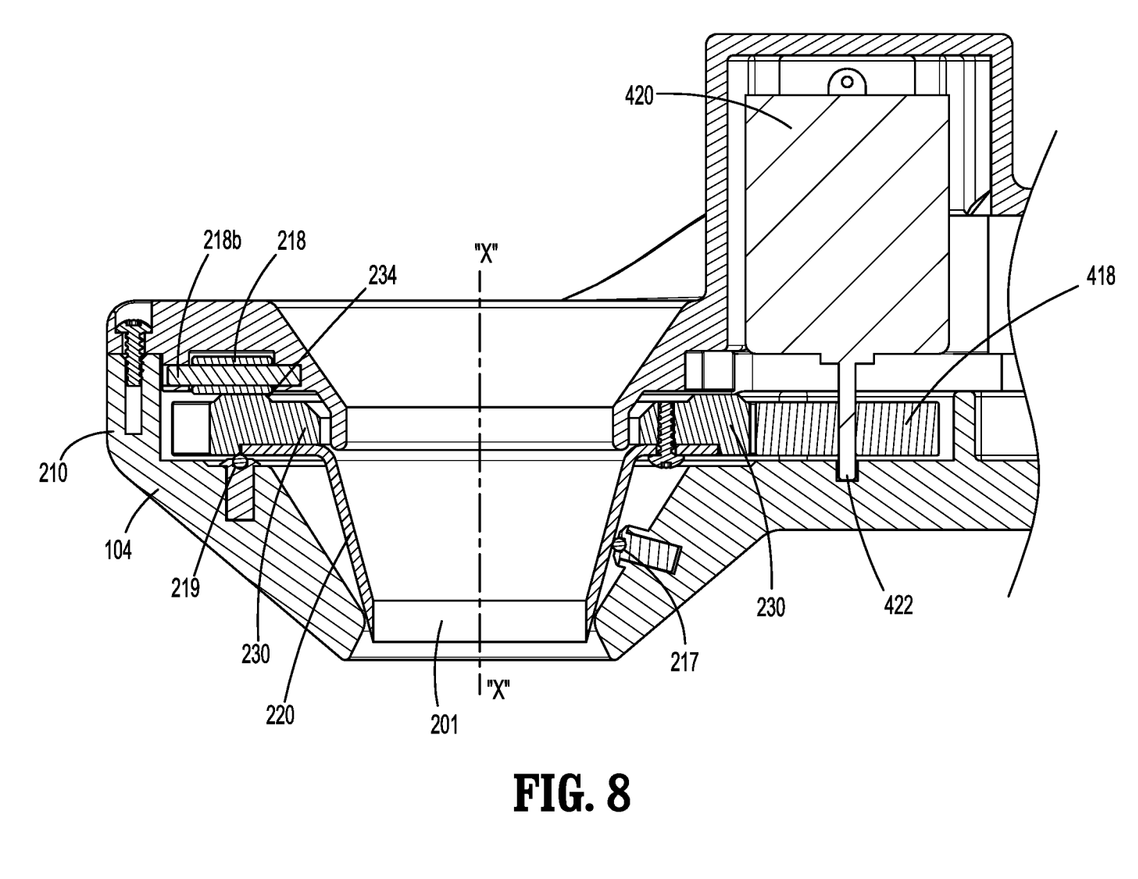
FIG. 8 is a cross-sectional view of the tissue dissector taken along section line 8-8 of FIG. 1.

With reference to FIG. 8, in order to further facilitate stability and/or rotation of the blade member 220, the annular body 210 may include additional bearings in various orientations. For example, a second bearing 219 may be provided. The second bearing 219 may be configured to engage the blade gear 230 on the side thereof where blade gear 230 engages the blade member 220. Under such a configuration, the blade gear 230 is supported between the axial bearings 218 and the second bearing 219. For example, the second bearing 219 may be disposed substantially parallel to a longitudinal axis "X-X" defined through the aperture 201. In order to further enhance stability of rotation of the blade assembly 250 (FIG. 3), the plurality of axial bearings 218 may be in registration with a plurality of second bearings 219. Additionally, the annular body 210 may further include a third bearing 217 configured to engage an outer surface of the blade portion 224 (FIG. 4) of the blade member 220 to facilitate rotation of the blade member 220. In particular, the third bearing 217 may be disposed at an acute angle relative to the axis "X-X". In order to enhance stability of the rotation of the blade member 220, a plurality of third bearings 217 may be provided about the blade member 220. It is contemplated that the tissue dissector 100 may include a control unit 700 (FIG. 3), e.g., a printed circuit board, to provide control functionality to the tissue dissector 100. It is further contemplated that handle portion 400 may include a battery pack 500 to supply power to the motor 420 and printed circuit board 700, although a cable (not shown) configured to connect to an external power source, e.g., standard electrical outlet, surgical generator, etc., is also contemplated. Under such a configuration, the tissue dissector 100 facilitates extraction of tissue by providing the aperture 201 having sufficient opening for tissue and a rotating blade edge 226 to cut tissue as it passes therethrough.

In use, the tissue dissector 100 is positioned with the dissector head portion 200 externally adjacent or partially extending into an opening, e.g., surgically created opening or naturally occurring orifice, providing access to an internal body cavity or organ. It is contemplated that the tissue dissector 100 may be used in conjunction with an access device, e.g., retractor, access port, or wound protector (not shown), in which case the dissector head portion 200 is positioned proximally adjacent or inserted partially through the access device anchored within the access opening at the surgical site. Once the dissector head portion 200 is positioned in the above manner, tissue dissector 100 is activated. The clinician may actuate the motor 420 by pushing an actuation button 430 (FIG. 1). Rotation of the output shaft 422 of the motor 420 rotates the blade member 220. In this manner, the clinician may cut and extract tissue by pulling the tissue up through aperture 201. The tissue dissector 100 may be utilized until the desired tissue is removed from the internal body cavity or organ. Once the desired tissue is removed, the tissue dissector 100 may be deactivated and removed from the surgical site. Thereafter, the tissue dissector 100 may be discarded, prepared for subsequent use, or sent for reprocessing.

Figure 9:
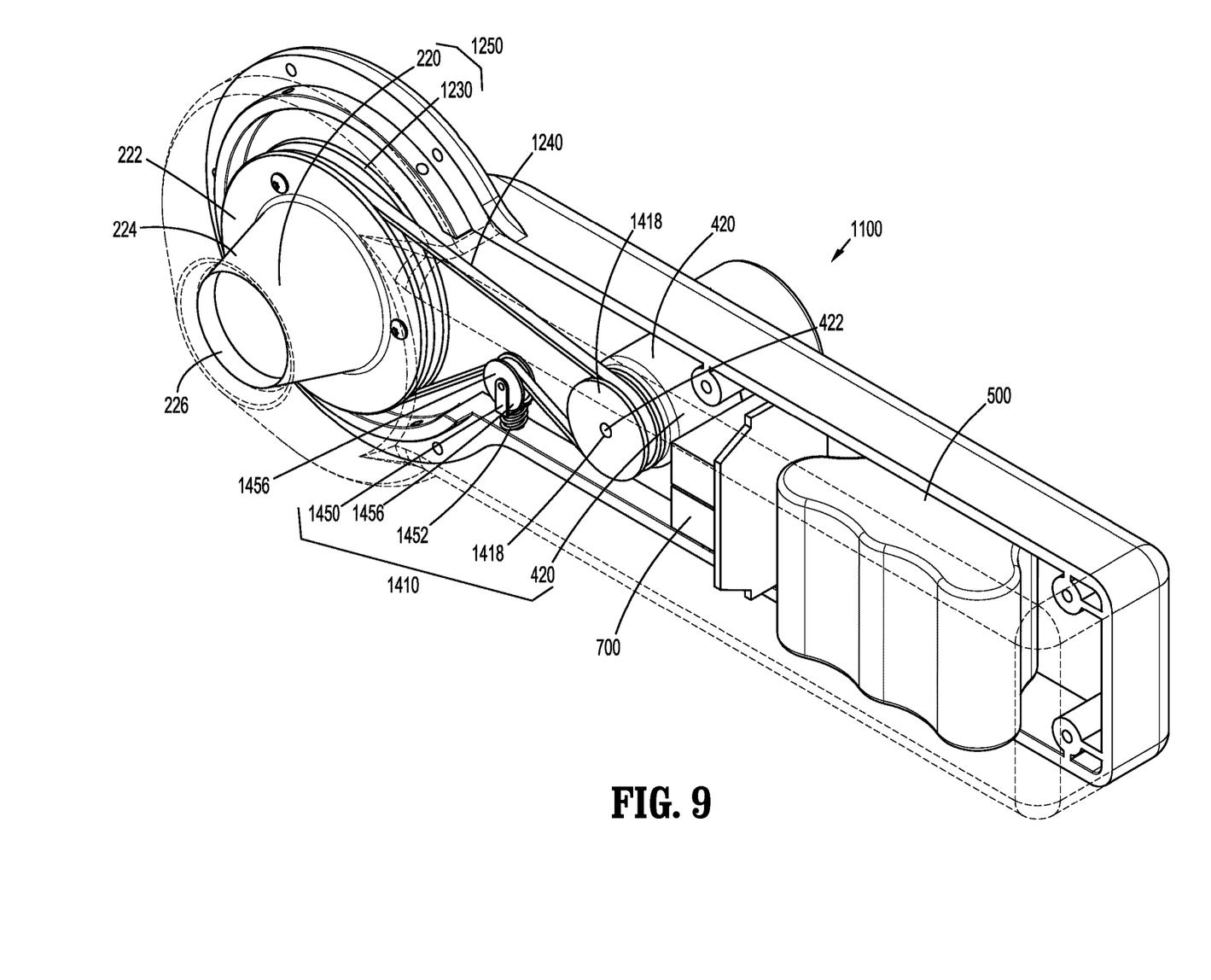
FIG. 9 is a bottom perspective view of another tissue dissector with a bottom housing half shown in phantom in accordance with the present disclosure.
Figure 10:
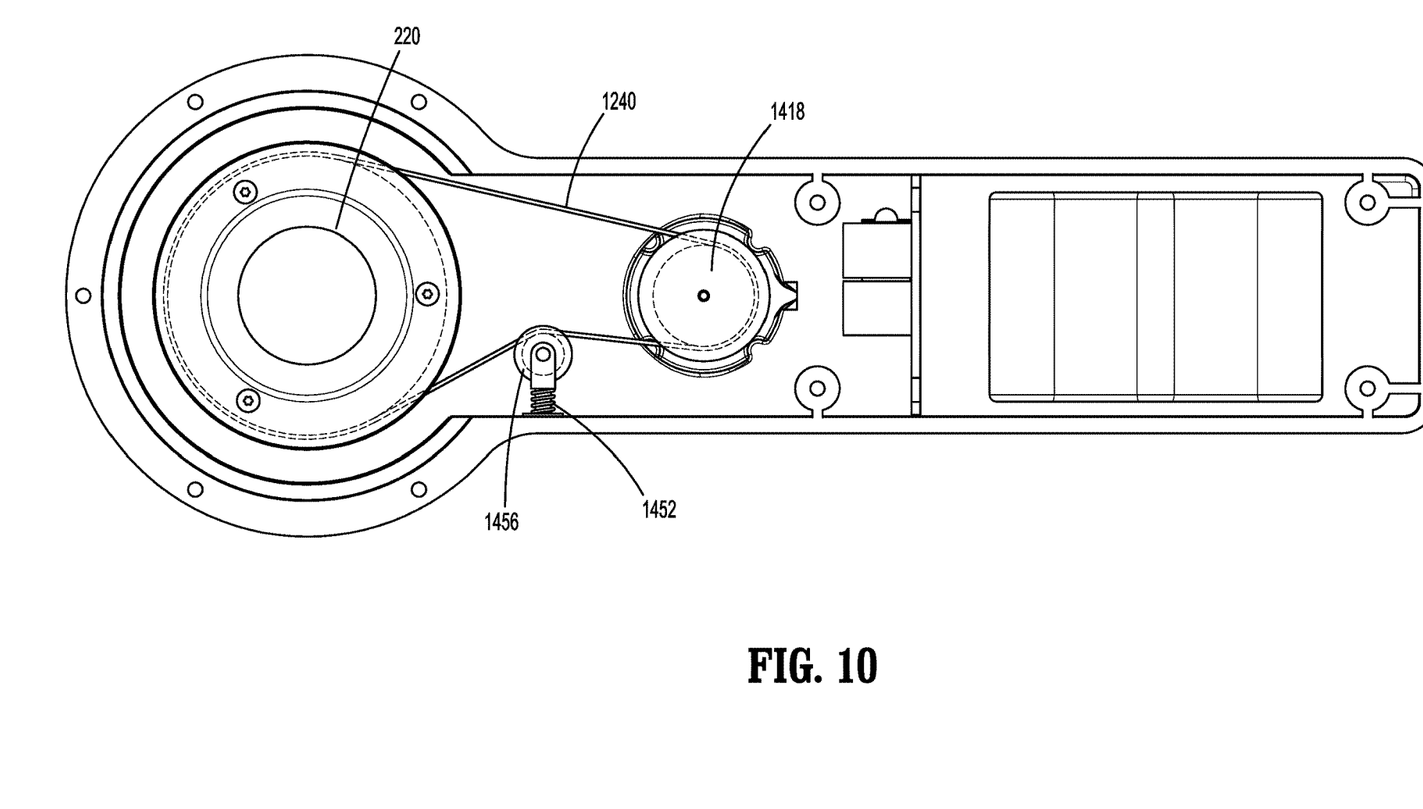
FIG. 10 is a top view of the tissue dissector of FIG. 9 with a top housing half removed.

With reference to FIGS. 9 and 10, there is provided a tissue dissector 1100 in accordance with another embodiment of the present disclosure. The tissue dissector 1100 is similar to the tissue dissector 100 and thus will only be discussed herein to the extent necessary to identify differences in construction and operation thereof. The tissue dissector 1100 includes an actuation assembly 1410 including a motor 420, a motor pulley 1418 operatively coupled with the motor 420, and a tensioner assembly 1450. The output shaft 422 of the motor 420 supports the motor pulley 1418 for concomitant rotation therewith. The blade member 220 of the blade assembly 1250 is secured with a blade pulley 1230 for concomitant rotation therewith. The blade pulley 1230 is operatively coupled with the motor pulley 1418 by a belt 1240. The belt 1240 further extends through the tensioner assembly 1450 having a biasing member 1452 configured to maintain desired tension in the belt 1240 by removing any slack in the belt 1240. Under such a configuration, actuation of the motor 420 drives the belt 1240, which, in turn, drives the blade pulley 1230. In this manner, the blade member 220 is rotated to cut tissue. The actuation assembly 1410 may protect the motor 420 in case of excess amount of torque, by causing belt slippage and inhibiting stalling of the motor 420. Further, such a configuration requires less precision and system alignment than a system that uses a gear assembly, which, in turn, requires, e.g., fewer friction reduction mechanisms. It is contemplated that the tissue dissector 1100 may include the battery pack 500 to supply power to the motor 420 and a printed circuit board 700 to control actuation of the motor 420 and supply of power from the battery pack 500. Use and operation of the tissue dissector 1100 is substantially identical to those of the tissue dissector 100, and thus, will be not be described herein.

Figure 11:
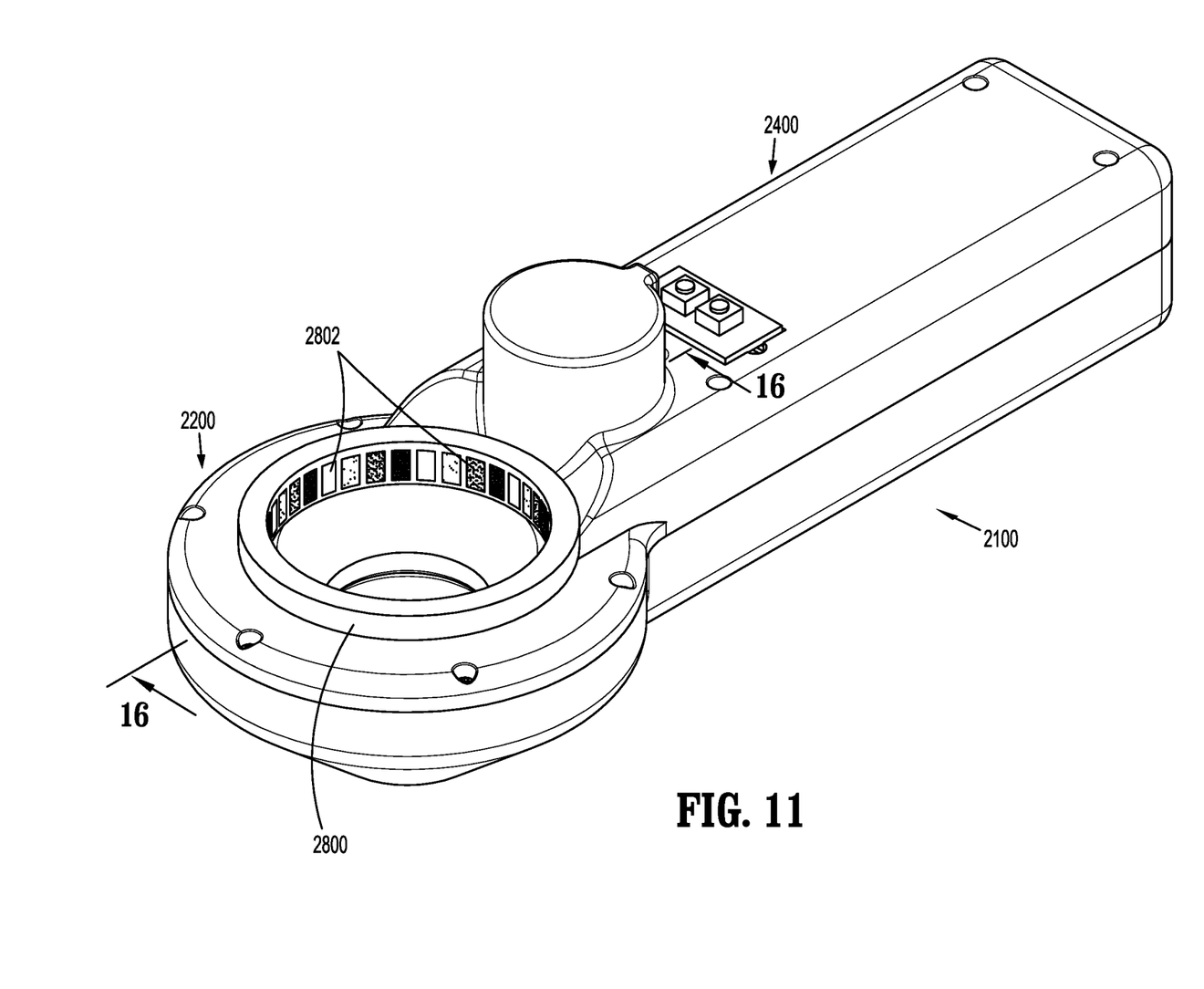
FIG. 11 is a perspective view of another tissue dissector in accordance with the present disclosure.
Figure 12:
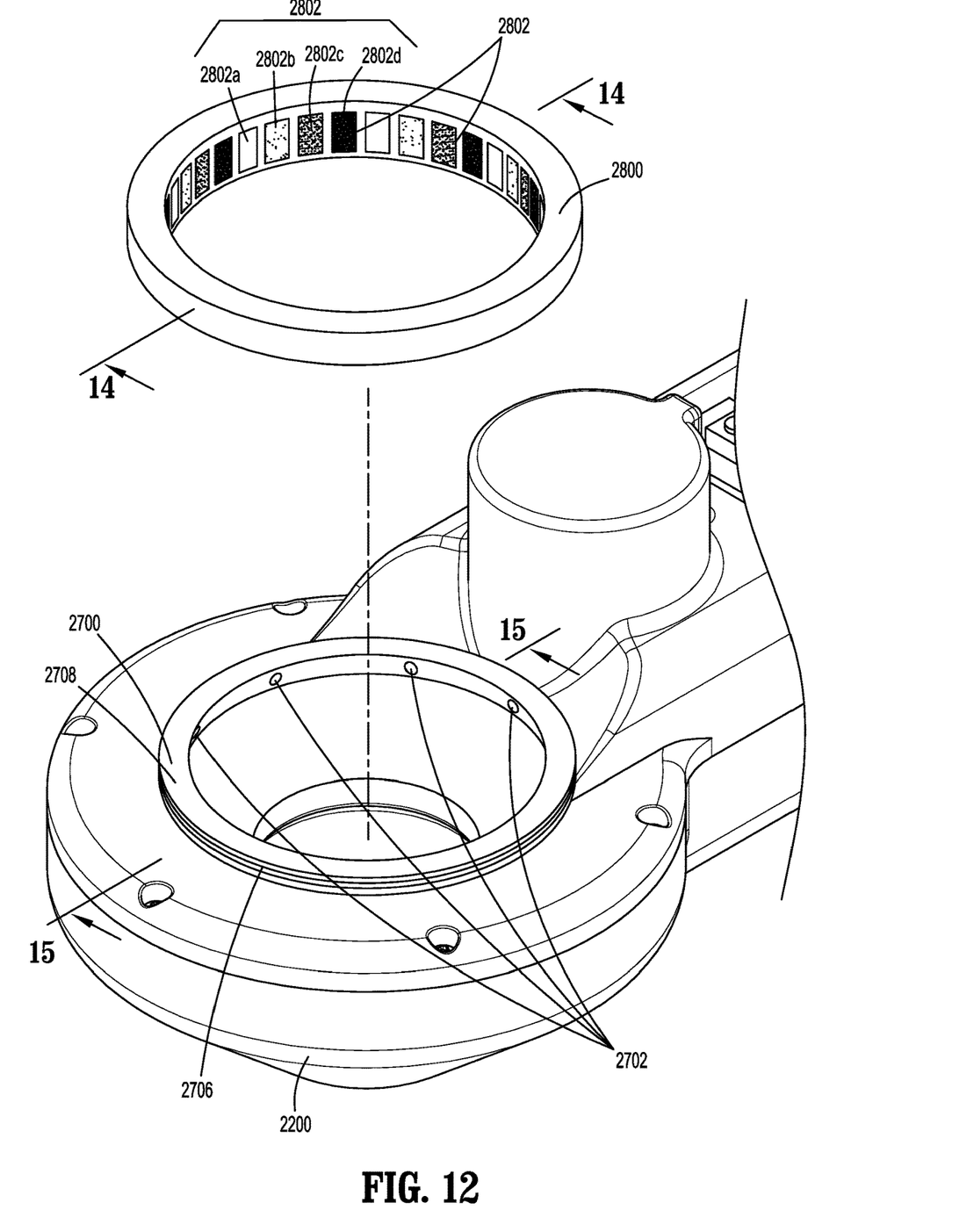
FIG. 12 is a partial perspective view of the tissue dissector of FIG. 11 with a window assembly separated.
Figure 13:
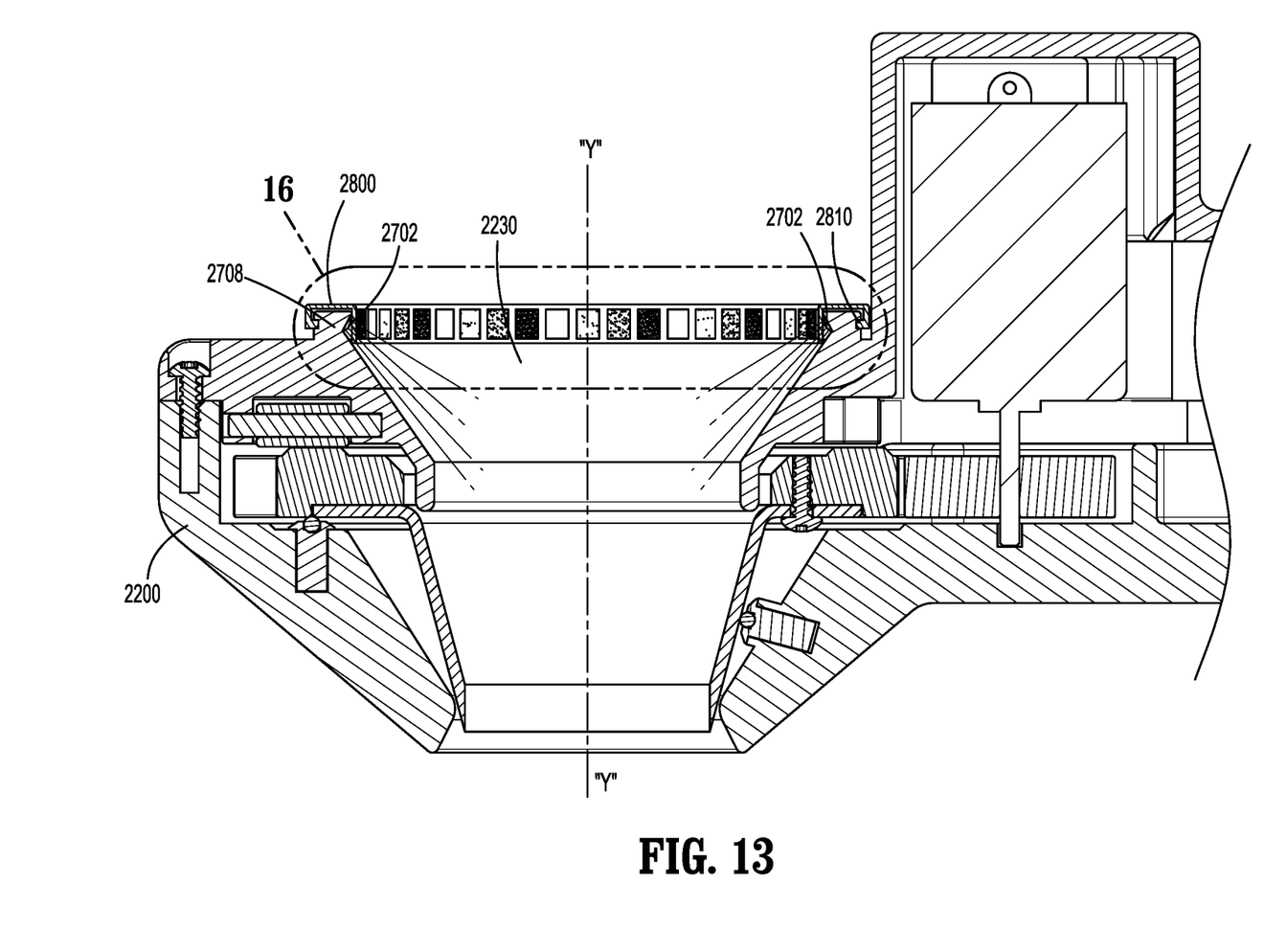
FIG. 13 is a partial side cross-sectional view of the tissue dissector of FIG. 11.

With reference now to FIGS. 11-13, there is provided a tissue dissector 2100 in accordance with another embodiment of the present disclosure. In the interest of brevity, portions of the tissue dissector 2100 substantially identical to the portions of the tissue dissectors 100, 1100 will not be described herein to avoid obscuring the present disclosure in unnecessary detail. The tissue dissector 2100 includes a handle portion 2400 and a dissector head portion 2200 attached to the handle portion 2400. The dissector head portion 2200 includes a lighting assembly 2700 including a plurality of light sources 2702 such as, e.g., light emitting diodes (LED), and a window assembly 2800 having a plurality of windows 2802. The lighting assembly 2700 improves visibility of the surgical site and/or tissue, and thus, may improve safety of the patient, increase cutting efficiency, and reduce extraction time of tissue.

With particular reference to FIG. 12, the lighting assembly 2700 may include a plurality of lights sources 2702 circumferentially arranged about a longitudinal axis "Y-Y" (FIG. 13) extending through an aperture 2230 (FIG. 13) defined by the dissector head portion 2200. For example, the lighting assembly 2700 may include a plurality of pairs of diametrically opposing light sources 2702. The dissector head portion 2200 includes a protruding lip 2708 supporting the plurality of light sources 2702. The protruding lip 2708 is configured to rotatably support the window assembly 2800 having the plurality of windows 2802.

Figure 14:
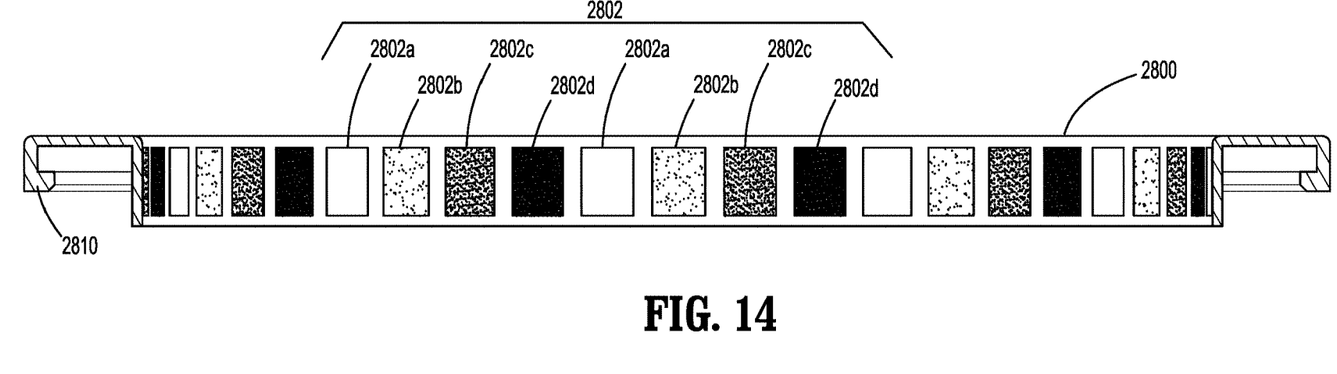
FIG. 14 is a side cross-sectional view of the window assembly of FIG. 12.
Figure 15:
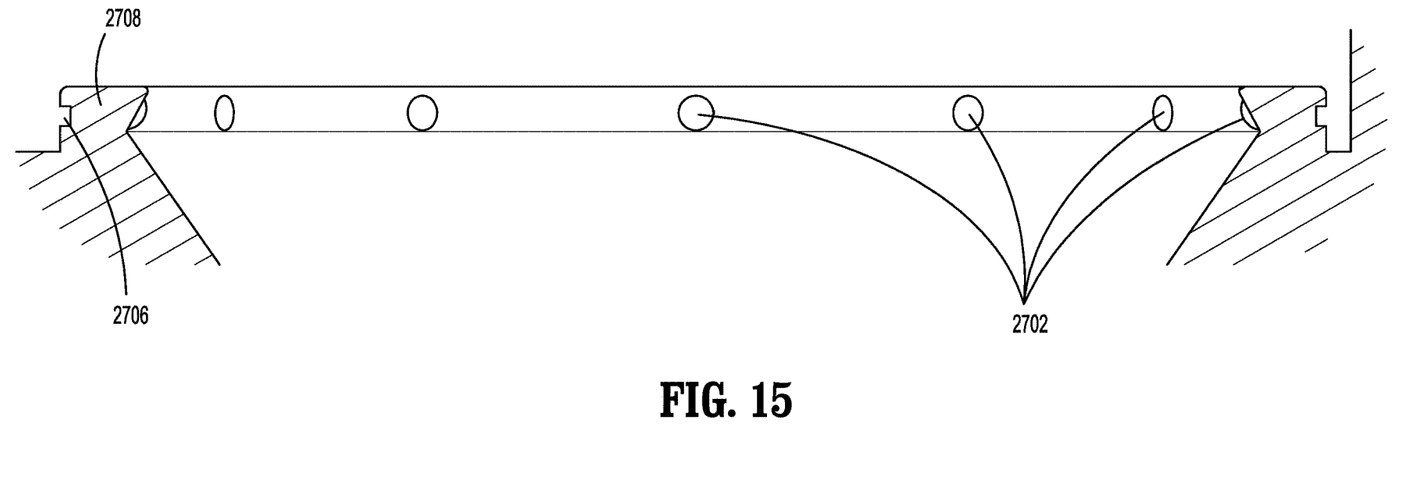
FIG. 15 is a partially enlarged side cross-sectional view of a dissector head portion of the tissue dissector of FIG. 11 taken along section line 15-15 of FIG. 12.
Figure 16:
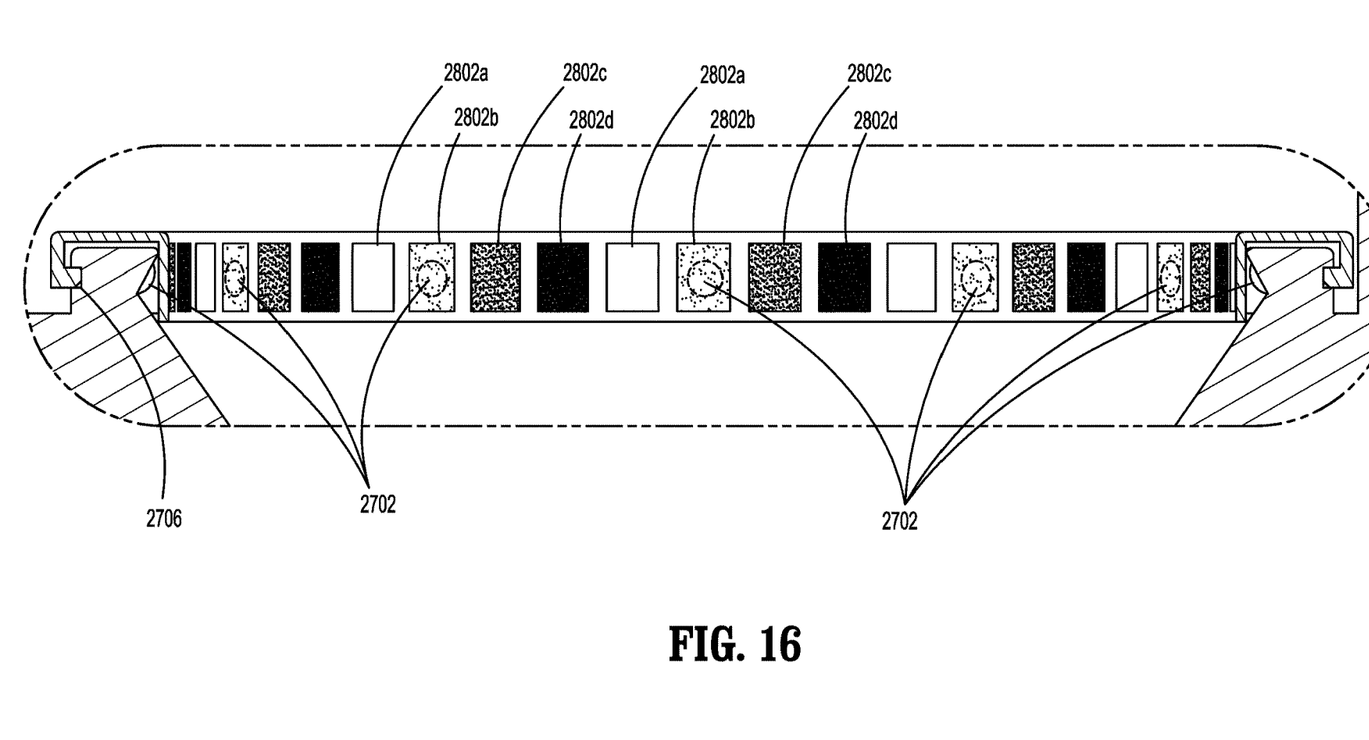
FIG. 16 is a side cross-sectional view of the area of detail of FIG. 13.

With particular reference to FIGS. 13 and 14, the plurality of windows 2802 may include different opacity. For example, the windows 2802a, 2802b, 2802c, 2802d may include opacity of 100%, 75%, 50%, and 25%, respectively. In this manner, brightness or intensity of the light sources 2702 may be adjustable by the clinician. With particular reference to FIGS. 14-16, for example, the windows 2802 may have repeating sequences of the opacity. It is contemplated that the circumferential spacing of the light sources 2702 (FIG. 5) and the repeating sequences of the opacity of the windows 2802 are such that when a light source 2702 is in registration with a window 2802 of a particular opacity, the other light sources 2702 are also in registration with the windows 2802 of the same opacity. With particular reference to FIG. 15, the protruding lip 2708 of the lighting assembly 2700 may include a slot 2706 configured to receive a finger 2810 (FIG. 14) of the window assembly 2800 to rotatably support the window assembly 2800 thereon. Alternatively, the window assembly 2800 may be threadably coupled to the lighting assembly 2700. In either configuration, the clinician may rotate the window assembly 2800 to selectively adjust the opacity of the windows 2802 for desired brightness or intensity of lighting by the light sources 2702.

Figure 17:
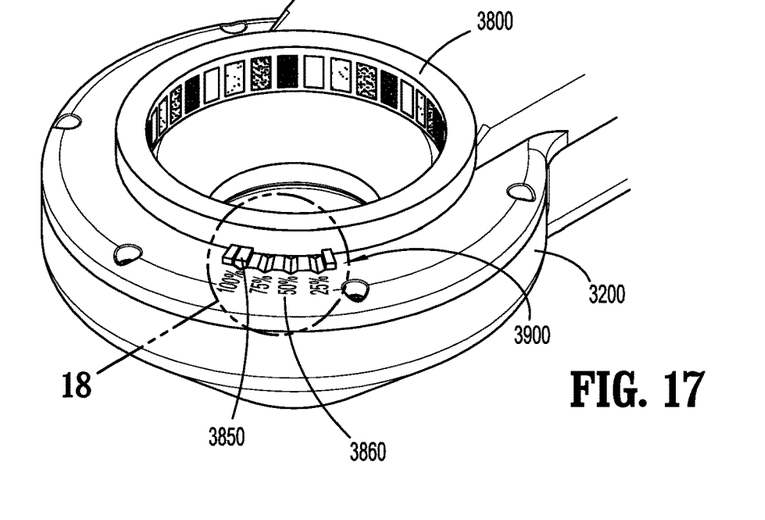
FIG. 17 is a perspective view of a window assembly configured for use with a tissue dissector in accordance with the present disclosure.
Figures 18, 19:
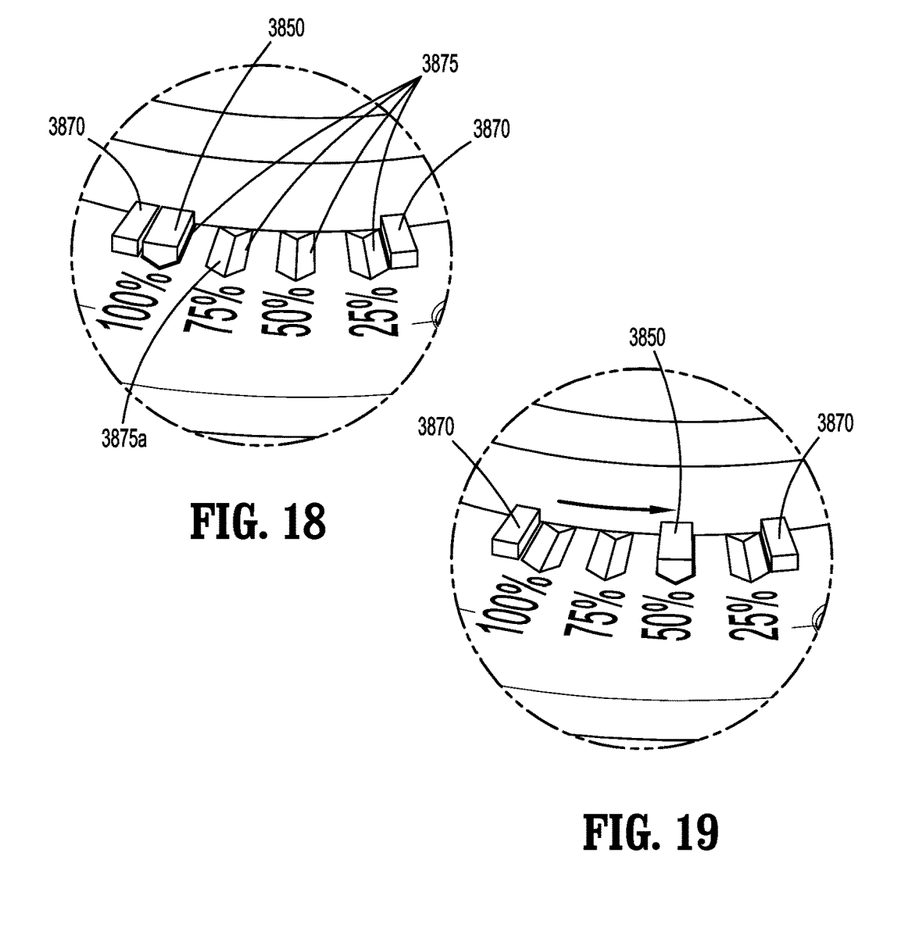
FIG. 18 is a perspective view of the area of detail of FIG. 17.
FIG. 19 is a perspective view of the area of detail of FIG. 17 illustrating rotation of the window assembly.

With reference now to FIGS. 17-19, there is illustrated a window assembly 3800 for use with the tissue dissector 2100 (FIG. 11) in accordance with an embodiment of the present disclosure. In the interest of brevity, portions of the window assembly 3800 substantially identical to the portions of the window assembly 2800 will not be described herein to avoid obscuring the present disclosure in unnecessary detail. The dissector head portion 3200 may include an opacity adjustment indicator 3900 to selectively adjust and visualize the opacity setting of the window assembly 3800. In particular, the window assembly 3800 includes an indicator 3850 that points to the indicia 3860 indicating current opacity setting when the indicator 3850 is selectively aligned with the indicia 3860. In this manner, the clinician can selectively choose registration of the plurality of light sources 2702 with the windows 2802a, 2802b, 2802c, 2802d of desired opacity. In addition, the dissector head portion 3200 may further include a pair of stops 3870 to limit rotation of the window assembly 2800 between the stops 3870. In particular, the stops 3870 are spaced apart such that rotation of the window assembly 3800 effects different opacity as discussed hereinabove such as, e.g., 100%, 75%, 50%, and 25%. Under such a configuration, the repeating sequences of the opacity of the windows 2802 are such that when a light source 2702 is in registration with a window 2802 of a particular opacity, the other light sources 2702 are also in registration with the windows 2802 of the same opacity. In addition, the dissector head portion 3200 and the indicator 3850 may include mating features. For example, the dissector head portion 3200 may define discrete grooves 3875 to engage the indicator 3850 to improve alignment of the light sources 2702 with the respective windows 2802. It is further contemplated that each groove 3875 may include ramp portions 3875a to facilitate slidable engagement of the indicator 3850 having, e.g., a complementary profile, to that of the groove 3875.

In this manner, the clinician may rotate the window assembly 3800 to selectively adjust the opacity of the windows 2802 for desired brightness or intensity of lighting by the light sources 2702.

The use and operation of the tissue dissector 2100 is substantially identical to those described hereinabove with respect to the tissue dissectors 100, 1100, and thus, will not be described herein.

It is contemplated that the tissue dissectors 100, 1100, 2100 may be used in conjunction with an access device, e.g., retractor, access port, or wound protector (not shown). For example, the frusto-conical shape of the blade member 220 may facilitate insertion partially into the wound protector. It is further contemplated that the battery pack 500 may be removably supported in the handle portion 400 of the tissue dissector 100, 1100, 2100. In addition, the tissue dissectors 100, 1100, 2100 may further include a printed circuit board 700 (FIG. 3) or other suitable control unit including a suitable microprocessor to control actuation of the motor 420 and supply of power from the battery pack 500. For example, the microprocessor of the printed circuit board 700 may monitor power consumption, e.g., current draw, by the motor 420 (which is indicative of torque output by the motor 420) and adjust the power supplied to the motor 420 accordingly to prevent damage or harm in the event aperture 201 is overfilled with tissue and/or tough tissue is encountered. Other safety features may likewise be implemented via the microprocessor of the printed circuit board 700 as cutting optimization features.

As an alternative to the handle portion 400 (FIG. 1) configured for manual grasping and manipulation during use, the tissue dissectors 100, 1100, 2100 may alternatively be configured for use with a robotic surgical system wherein the dissector head portion 200, 3200 are configured to engage a robotic arm of the robotic surgical system in a similar manner as detailed above with respect to engagement of the dissector head portion 200, 3200 with the handle portion 400. The robotic surgical system may employ various robotic elements to assist the surgeon and allow remote operation (or partial remote operation). More specifically, various robotic arms, gears, cams, pulleys, electric and mechanical motors, etc. may be employed for this purpose and may be designed with the robotic surgical system to assist the surgeon during the course of an operation or treatment. The robotic surgical system may include remotely steerable systems, automatically flexible surgical systems, remotely flexible surgical systems, remotely articulating surgical systems, wireless surgical systems, modular or selectively configurable remotely operated surgical systems, etc.

The robotic surgical system may be employed with one or more consoles that are next to the operating theater or located in a remote location. In this instance, one team of surgeons or nurses may prep the patient for surgery and configure the robotic surgical system with the surgical device disclosed herein while another surgeon (or group of surgeons) remotely control the surgical device via the robotic surgical system. As can be appreciated, a highly skilled surgeon may perform multiple operations in multiple locations without leaving his/her remote console which can be both economically advantageous and a benefit to the patient or a series of patients.

The robotic arms of the robotic surgical system are typically coupled to a pair of master handles by a controller. The handles can be moved by the surgeon to produce a corresponding movement of the working ends of any type of surgical instrument (e.g., end effectors, graspers, knifes, scissors, cameras, fluid delivery devices, etc.) which may complement the use of the tissue resecting devices described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as examples of particular embodiments. Those skilled in the art will envision other modifications within the scope and spirit of the claims appended hereto.

Although the foregoing disclosure has been described in some detail by way of illustration and example, for purposes of clarity or understanding, it will be obvious that certain changes and modifications may be practiced within the scope of the appended claims.

What is claimed is:

1. A tissue dissector comprising:
    a handle portion including an actuation assembly having an actuator; and
    a head portion including an annular body having a blade assembly rotatably supported in the annular body, the blade assembly including a blade member defining an aperture configured to receive tissue therethrough, the blade member operatively coupled with the actuator for rotation about a central axis defined by the aperture, wherein:
        the handle portion and head portion define a longitudinal axis that is disposed at an angle relative to the central axis,
        the blade assembly further includes a blade gear secured with the blade member for concomitant rotation therewith, the blade gear operatively coupled with the actuator of the actuation assembly,
        the blade member includes a support portion and a blade portion extending from the support portion, the support portion in a planar contact with the blade gear, and
        the head portion further includes a third bearing configured to engage the blade portion of the blade member, wherein the third bearing defines an acute angle with respect to an axis extending through the aperture.

2. The tissue dissector according to claim 1, wherein the blade portion has a frusto-conical shape.

3. The tissue dissector according to claim 1, wherein the actuation assembly further includes a transmission gear coupled with an output shaft of the actuator and configured to engage the blade gear such that actuation of the actuator imparts rotation to the blade member.

4. The tissue dissector according to claim 1, wherein the head portion further includes inner and outer walls defining a circular groove therebetween, wherein at least a portion of the blade gear is rotatably disposed within the circular groove.

5. The tissue dissector according to claim 4, wherein the head portion further includes a plurality of axial bearings circumferentially arranged in the circular groove of the head portion, the blade gear rotatably supported in the circular groove.

6. The tissue dissector according to claim 5, wherein the head portion further includes a plurality of second bearings configured to engage the blade gear, the plurality of second bearings is disposed substantially parallel to an axis extending through the aperture of the blade member.

7. The tissue dissector according to claim 6, wherein the blade gear is rotatably interposed between the plurality of axial bearings and the plurality of second bearings.

8. The tissue dissector according to claim 1, wherein the handle portion further defines a battery pack to supply power to the actuator.

9. The tissue dissector according to claim 8, wherein the battery pack is removably disposed within the handle portion.

* * * * *